United States Patent [19]
Grollier et al.

[11] Patent Number: 4,885,006
[45] Date of Patent: * Dec. 5, 1989

[54] PROCESS FOR DYEING KERATINOUS FIBRES WITH INDOLE DERIVATIVES COMBINED WITH AN IODIDE

[75] Inventors: Jean F. Grollier, Paris; Didier Garoche, Levallois-Perret, both of France

[73] Assignee: L'Oreal, Paris, France

[*] Notice: The portion of the term of this patent subsequent to Feb. 14, 2006 has been disclaimed.

[21] Appl. No.: 121,890

[22] Filed: Nov. 17, 1987

[30] Foreign Application Priority Data

Nov. 17, 1986 [LU] Luxembourg .............................. 86668

[51] Int. Cl.⁴ .............................................. A61K 7/13
[52] U.S. Cl. ............................................ 8/423; 8/406; 8/634
[58] Field of Search .................. 8/404, 405, 406, 423, 8/634

[56] References Cited

U.S. PATENT DOCUMENTS

| | | | |
|---|---|---|---|
| 1,677,508 | 7/1928 | Windgradoff | 8/404 |
| 2,934,396 | 4/1960 | Charle et al. | 8/11 |
| 3,976,639 | 8/1976 | Batcho | 260/240 R |
| 4,208,183 | 6/1980 | Grollier et al. | 8/409 |

FOREIGN PATENT DOCUMENTS

| | | |
|---|---|---|
| 2028818 | 12/1970 | Fed. Rep. of Germany . |
| 1166172 | 11/1958 | France . |
| 2390158 | 12/1978 | France . |
| 887579 | 1/1962 | United Kingdom . |
| 2132342 | 7/1984 | United Kingdom . |
| 2185498 | 7/1987 | United Kingdom . |
| 2186891 | 8/1987 | United Kingdom . |
| 2187456 | 9/1987 | United Kingdom . |

*Primary Examiner*—Paul Lieberman
*Assistant Examiner*—Linda D. Skaling
*Attorney, Agent, or Firm*—Cushman, Darby & Cushman

[57] ABSTRACT

Process for dyeing human keratinous fibres, consisting in applying on these fibres at least least one composition (A) containing, in a cosmetically acceptable medium, one or more indole derivatives corresponding to the formula (I)

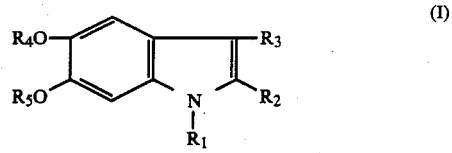

in which:
$R_1$ denotes a hydrogen atom, a lower $C_1$–$C_6$ lower akly group or a group —$SiR_9R_{10}R_{11}$;
$R_2$ and $R_3$, which may be identical or different, denote a hydrogen atom, a $C_1$–$C_5$ lower alkyl group, a carboxyl group, a lower alkoxycarbonyl group wherein the alkoxy moiety contains 1 to 6 carbon atoms, or a group —$COOSiR_9R_{10}R_{11}$;
$R_4$ and $R_5$, which may be identical or different, denote a hydrogen atom, a $C_1$–$C_{20}$ linear or branched alkyl group, a formyl group, a linear or branched $C_2$–$C_{20}$ acyl group, a linear or branched $C_3$–$C_{20}$ alkenoyl group, a group —$SiR_9R_{10}R_{11}$, a group —$P(O)(OR_6)_2$ or a group $R_6OSO_2$—, or alternatively $R_4$ and $R_5$, together with the oxygen atoms to which they are attached, form a ring optionally containing a carbonyl group, a methylene group, a thiocarbonyl group or one of the following groups; $>P(O)OR_6$, or $>CR_7R_8$;
$R_6$ and $R_7$ denoting a hydrogen atom or $C_1$–$C_6$ lower alkyl group, $R_8$ denoting a $C_1$–$C_6$ lower alkoxy group or a mono- or di-$C_1$–$C_6$ alkylamino group, $R_9$, $R_{10}$ and $R_{11}$, which may be identical or different, denoting $C_1$–$C_6$ linear or branched alkyl groups, and the corresponding salts of alkali metals, alkaline-earth metals and amines, at least one of the radicals $R_1$ to $R_5$ being other than hydrogen,
in combinations:
either (a) with iodide ions, or (b) with a solution of hydrogen peroxide at a pH of between 3.5 and 7, the application of the composition (A) being preceded or followed by the application of composition (B) which contains, in a cosmetically acceptable medium, either (a) hydrogen peroxide at a pH of between 2 and 7 when the composition (A) contains iodide ions, or (b) iodide ions when the composition (A) contains hydrogen peroxide.

21 Claims, No Drawings

PROCESS FOR DYEING KERATINOUS FIBRES WITH INDOLE DERIVATIVES COMBINED WITH AN IODIDE

The present invention relates to a new process for dyeing human keratinous fibres with indole derivatives, and to the compositions employed in this process.

It is well known that the natural biosynthesis of eumelanins from tyrosine takes place in several stages. One of these consists in the formation of 5,6-dihydroxyindole, which is oxidized to give a pigment which is one of the main constituents of eumelanin.

Many processes for dyeing hair employing 5,6-dihydroxyindole and indole derivatives have already been proposed in the past.

Thus, in French Patent 1,166,172, a solution of 5,6-dihydroxyindole at acid pH is applied on the hair for 5 to 60 minutes and, without rinsing and after towel-drying, the colour is developed by means of an oxidizing agent which can be, in particular, hydrogen peroxide.

In French Patent 1,133,594, an alkaline solution of 5,6-dihydroxyindole, optionally containing an oxidizing agent or an oxidation catalyst, is applied on the hair. Various oxidizing agents including hydrogen peroxide and oxidation catalysts such as cupric chloride are envisaged.

It is also possible, according to this process, to work in two stages, the application of 5,6-dihydroxyindole in alkaline medium being followed by a rinse and development with an oxidation catalyst.

In French Patent Application 2,536,993, a dyeing process in several stages separated by rinses has also been recommended, this process consisting in applying, in one stage, a solution of a metal salt at alkaline pH, and in another stage a solution of 5,6-dihydroxyindole.

After rinsing or shampooing, these two stages are followed or otherwise by the application of hydrogen peroxide in order to adjust the final shade by lightening.

These processes of the prior art contain various drawbacks, inasmuch as they lead either to shades having poor intensities despite long exposure times, or to the production of intense shades but which require a long exposure time and lead to a surface dyeing having very poor fastness. The use of certain metal salts of groups III to VIII of the Periodic Classification, which are not always shown to be harmless, may lead, under the conditions of use, to modification of the cosmetic and mechanical properties of the hair fibre.

The compositions based on 5,6-dihydroxyindole and some of its derivatives possess, moreover, problems of stability on storage, in particular in alkaline medium.

Under the conditions used in the prior art described above, the light shades obtained result chiefly from a partial destruction of the pigments formed, and not from the molecular nature of the 5,6-dihydroxyindole used. In effect, the light shades originate from the bleaching of the pigment formed, this bleaching being caused by the use of an excess of hydrogen peroxide. Moreover, this excess of hydrogen peroxide may, in addition, possess the drawback of degrading the hair fibre.

A dyeing process involving certain methylated derivatives of 5,6-dihydroxyindole has already been proposed in French Patent 1,264,707 for obtaining lighter shades than those obtained with 5,6-dihydroxyindole. The light shades then obtained result from the molecular nature of the methylated derivatives of 5,6-dihydroxyindole used.

However, this process requires a long exposure time in order to develop the desired shade and leads to a surface dyeing having very poor fastness.

The Applicant has now discovered, and this forms the subject of the invention, a process for dyeing human keratinous fibres employing indole derivatives, enabling intense colours to be obtained without degrading the hair, in very short exposure times. The shades obtained, dark or light, show exceptional fastness to washing and light.

Another subject of the invention consists of compositions employed in this process, as well as the multicomponent dyeing kits employing the different compounds.

Other subjects of the invention will emerge upon reading the description and the examples which follow.

The process for dyeing human keratinous fibres, and especially hair, according to the invention, is essentially characterized in that there is applied on these fibres at least one composition (A) containing, in a cosmetically acceptable medium, one or more indole derivatives of the formula (I)

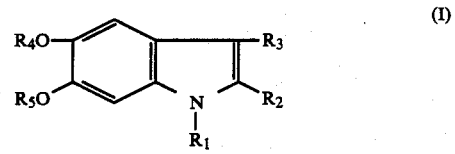

in which $R_1$ denotes a hydrogen atom, a $C_1$–$C_6$ lower alkyl group or a group —$SiR_9R_{10}R_{11}$;

$R_2$ and $R_3$, which may be identical or different, denote a hydrogen atom, a $C_1$–$C_6$ lower alkyl group, a carboxyl group, a lower alkoxycarbonyl group wherein the alkoxy moiety has 1 to 6 carbon atoms, a group —$COOSiR_9R_{10}R_{11}$;

$R_4$ and $R_5$, which may be identical or different, denote a hydrogen atom, a $C_1$–$C_{20}$ linear or branched alkyl group, a formyl group, a linear or branched $C_2$–$C_{20}$ acyl group, a linear or branched $C_3$–$C_{20}$ alkenoyl group, a group —$SiR_9R_{10}R_{11}$, a group —$P(O)(OR_6)_2$ or a group $R_6OSO_2$—, or alternatively $R_4$ and $R_5$, together with the oxygen atoms to which they are attached, form a ring optionally containing a carbonyl group, a methylene group, a thiocarbonyl group or one of the following groups: $>P(O)OR_6$, or $>CR_7R_8$;

$R_6$ and $R_7$ denoting a hydrogen atom or a $C_1$–$C_6$ lower alkyl group, $R_8$ denoting a $C_1$–$C_6$ lower alkoxy group or a mono-or di $C_1$–$C_6$ alkylamino group; $R_9$, $R_{10}$ and $R_{11}$, which may be identical or different, denoting a $C_1$–$C_6$ linear or branched lower alkyl groups, at least one of the radicals $R_1$ to $R_5$ being other than hydrogen, and the addition salts with inorganic or organic acids such as, for example, the hydrochlorides and hydrobromides, as well as the corresponding salts of alkali metals, alkaline earth metals or amines, in combination either (a) with iodide ions, or (b) with a solution of hydrogen peroxide at a pH of between 3.5 and 7, and in that the application of this composition (A) is preceded or followed by the application of a composition (B) which contains, in a cosmetically acceptable medium, either (a) hydrogen peroxide at a pH of between 2 and 7 when the composition (A) contains iodide ions, or (b) iodide ions when the composition (A) contains hydrogen peroxide.

In the compounds of formula I defined above, the lower alkyl or lower alkoxy group preferably denotes a group having 1 to 6 carbon atoms.

Among the compounds of formula I, defined above, the compounds that are especially preferred are those corresponding to the formula II:

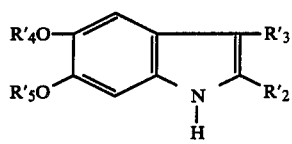

in which $R'_2$ and $R'_3$, which may be identical or different, denote a hydrogen atom, a $C_1$–$C_6$ lower alkyl group, a carboxyl group, a lower alkoxycarbonyl group in which the alkoxy group is a $C_1$–$C_6$ group, $R'_4$ and $R'_5$, which may be identical or different, denote a hydrogen atom, a $C_1$–$C_6$ lower alkyl group, a $C_2$–$C_{20}$, and preferably $C_2$–$C_{14}$, linear acyl group, or a trimethylsilyl group, or alternatively $R'_4$ and $R'_5$, together with the oxygen atoms to which they are attached, form a methylenedioxy or carbonyldioxy ring, at least one of $R'_4$ or $R'_5$ being different from hydrogen.

Among the compounds of formula I that are especially preferred, there may be mentioned 5-methoxy-6-hydroxyindole, 3-methyl-5,6-dihydroxyindole, 2-methyl-5,6-dihydroxyindole, 5,6-bis(trimethylsilyloxy)indole, 5-(or 6-)myristoyloxy-6-(or 5-)hydroxyindole, 5,6-(methylenedioxy)indole, 5-acetoxy-6-hydroxyindole, 2-ethoxycarbonyl-5,6-dihydroxyindole, 5-hydroxy-6-methoxyindole, 5,6-carbonyldioxyindole and 2-carboxy-5,6-dihydroxyindole, 2,3-dimethyl 5,6-dihydroxyindole.

The composition (B), when it contains iodide ions in an aqueous medium optionally containing one or more solvents, has a pH of between 3 and 11.

The iodide ion is preferably present in the form of an alkali metal, alkaline earth metal or ammonium iodide, and more especially potassium or ammonium iodide.

An especially preferred embodiment of the invention consists in applying, during the first stage, the composition (A) containing the indole derivative of formula I and iodide ions in the form of alkali metal or alkaline earth metal iodide or ammonium, and then, in a second stage, the composition (B) containing hydrogen peroxide.

The fibres may optionally be rinsed between the two stages.

The subject of the invention is also a composition designed to be used in the dyeing of human keratinous fibres, and more especially hair, containing one or more indole derivatives corresponding to the formula I and iodide ions in the preferred form of alkali metal or alkaline earth metal or ammonium iodide at a pH of between 3.5 and 7 when the aqueous medium consists of water or a water/solvent(s) mixture. Such a composition is especially stable on storage.

In the process and the compositions according to the invention, the indole derivative(s) of formula (I) may be used alone or in the form of a mixture with 5,6-dihydroxyindole itself.

In the compositions employed in the process according to the invention, the indole derivative or derivatives is/are generally present in proportions of between 0.01 and 5% by weight, preferably between 0.03 and 2.5% by weight, based on the total weight of the composition. The proportion of iodide in the compositions of the invention is preferably between approximately 0.007 and 4% by weight based on the total weight of the composition, this concentration being expressed as $I^-$ ions.

The content of hydrogen peroxide in the hydrogen peroxide solutions used according to the invention is between 1 and 40 volumes, preferably between 2 and 20 volumes and more especially between 3 and 10 volumes.

The process is carried out with exposure times, for the different compositions applied in each of the different stages of the process, of between 10 seconds and 45 minutes, and preferably of the order of 2 to 10 minutes.

Dark or light colours are obtained in relatively short times, of the order of 2 to 15 minutes.

The compositions used according to the invention can take various forms that are customarily used for hair dyeing, such as liquids which are gelled or thickened to a greater or lesser extent, creams or emulsions, or any other form suitable for carrying out hair dyeing.

The dyeing compositions employed in the process which forms the subject of the invention generally contain a cosmetic medium which is either aqueous, or based on solvent(s), or based on a water/solvent(s) mixture, the solvent being an organic solvent which is acceptable from the cosmetic standpoint, chosen from ethyl alcohol, isopropyl alcohol and tert-butyl alcohol, ethylene glycol monomethyl, monoethyl and monobutyl ethers, and ethylene glycol monoethyl ether acetate.

The preferred solvent is ethyl alcohol.

When the cosmetic medium is a water/solvent(s) mixture, the solvents are present in concentrations that are preferably between 0.5 and 75%, and especially between 2 and 50%, by weight, based on the total weight of the composition.

The composition can also contain fatty amides such as mono- and diethanolamides of acids derived from copra, of lauric acid or of oleic acid, at concentrations of between 0.05 and 10% by weight.

The compositions used according to the invention can contain anionic, cationic, nonionic or amphoteric surfactants, or mixtures thereof. These surfactants are preferably used in proportions of between 0.1 and 50% by weight based on the total weight of the composition, and advantageously between 1 and 20% by weight.

The compositions defined above may be thickened with thickening agents such as sodium alginate, gum arabic, guar gum, biopolymers such as xanthan gum, cellulose derivatives such as methylcellulose, hydroxyethylcellulose, hydroxypropylmethylcellulose and the sodium salt of carboxymethylcellulose, and polymers of acrylic acid. It is also possible to use inorganic thickening agents such as bentonite. These thickeners are used alone or in the form of a mixture, and are preferably present in proportions of between 0.1 and 5% by weight based on the total weight of the composition, and advantageously between 0.5 and 3%.

The alkalinizing agents which are usable in the compositions of the invention can be, in particular, amines such as alkanolamines, alkylamines and alkali metal or ammonium hydroxides or carbonates. The acidifying agents which are usable in the compositions according to the invention may be chosen from lactic acid, acetic acid, tartaric acid, phosphoric acid, hydrochloric acid and citric acid. It is possible to use any other alkalinizing or acidifying agent which is acceptable from the cosmetic standpoint.

It is possible, optionally, to add an agent for swelling the hair, such as, for example, urea, to each of the compositions.

The compositions used according to the invention may further contain 5,6-dihydroxyindole.

The compositions employed in the process according to the invention can contain, in addition, various additives customarily used in cosmetics, such as perfumes, sequestering agents, film-forming products or treatment agents, dispersants, hair conditioning agents, preservatives or opacifiers.

For the purpose of carrying out the process according to the invention, the compositions may be packaged in multi-compartment devices, also known as dyeing kits or outfits, comprising all the components designed to be applied on the hair for a single dyeing treatment, in successive applications, with or without premixing. Such devices are known per se and may comprise a first compartment containing the indole derivative or derivatives as defined above, in the presence of iodide ions, in a cosmetically acceptable medium, and in a second compartment a solution of hydrogen peroxide at a pH of between 2 and 7.

If the cosmetically acceptable medium in the first compartment is an aqueous medium optionally containing solvents, the pH is adjusted between 3.5 and 7.

According to another embodiment, the hair dyeing kit comprises a first compartment enclosing a composition containing iodide ions in a cosmetically acceptable medium, a second compartment enclosing a composition containing the indole derivative or derivatives as defined above in a cosmetically acceptable medium, and a third compartment enclosing a 1- to 40-volumes solution of hydrogen peroxide at a pH of between 2 and 7, the composition contained in the third compartment being designed to be mixed at the time of use with the content of the second compartment.

In this second embodiment, if the medium in the first and the second compartment is an aqueous medium optionally containing one or more solvents, the pH of the composition in the first compartment is between 3 and 11 and that in the second compartment is between 3.5 and 7.

The multi-compartment devices that are used according to the invention may be equipped with means, known per se, for mixing at the time of use, and be packaged under an inert atmosphere.

The compositions according to the invention may be used for dyeing natural or already dyed hair, permanent-waved or otherwise, or hair that has been strongly or lightly bleached and, if desired, permanent-waved.

The examples which follow are designed to illustrate the invention without, however, being limiting in nature.

EXAMPLE 1

Permanent-waved hair that is 90% white is dyed by successively applying two compositions without performing intermediate rinsing.

The hair is impregnated for 5 minutes with the following composition (A):

| 5-Methoxy-6-hydroxyindole | 1 g |
|---|---|
| Potassium iodide | 1 g |
| Ethyl alcohol | 50 g |
| Water qs | 100 g |
| Natural pH 7.0 | |

After towel-drying and without intermediate rinsing, a 20-volumes solution of hydrogen peroxide (B) at pH 3 is applied, the hair being massaged for 5 minutes.

After rinsing with water, a dark ash-blond colour is obtained.

EXAMPLE 2

Permanent-waved hair that is 90% white is dyed by successively applying two compositions without performing intermediate rinsing.

The hair is impregnated for 5 minutes with the following composition:

| 3-Methyl-5,6-dihydroxyindole | 1 g |
|---|---|
| Potassium iodide | 1 g |
| Ethyl alcohol | 10 g |
| Water qs | 100 g |
| Citric acid qs pH 4.3 | |

After towel-drying and without performing an intermediate rinse, a 20-volumes solution of hydrogen peroxide at pH 3 is applied, the hair being massaged for 5 minutes.

After rinsing with water, a midnight blue colour is obtained.

EXAMPLE 3

Permanent-waved hair that is 90% white is dyed by successively applying two compositions without performing intermediate rinsing.

The hair is impregnated for 5 minutes with the following composition (A):

| 2-Methyl-5,6-dihydroxyindole | 0.5 g |
|---|---|
| Potassium iodide | 0.5 g |
| Ethyl alcohol | 10.0 g |
| Water qs | 100.0 g |
| Natural pH 6 | |

After towel-drying and without intermediate rinsing, a 20-volumes solution of hydrogen peroxide (B) at pH 3 is applied, the hair being massaged for 5 minutes.

After rinsing with water, a copper-blonde colour is obtained.

EXAMPLE 4

Natural hair that is 90% white is dyed by successively applying two compositions without performing intermediate rinsing.

The hair is impregnated for 4 minutes with the following composition:

| 5-Methoxy-6-hydroxyindole | 2 g |
|---|---|
| Potassium iodide | 2 g |
| Ethyl alcohol | 10 g |
| Sodium lauryl ether sulphate oxyethylenated with 2 moles of ethylene oxide | 4.5 g |
| Water qs | 100 g |
| Natural pH 5.6 | |

Without performing intermediate rinsing, a 12.5-volumes solution of hydrogen peroxide at pH 3 is then applied, the hair being massaged for 5 minutes.

After rinsing with water, an irridescent natural chestnut colour is obtained.

EXAMPLE 5

Permanent-waved hair that is 90% white is dyed by successively applying two compositions and performing intermediate rinsing.

The hair is impregnated for 5 minutes with a gel having the following composition (A):

| | |
|---|---|
| 5-Methoxy-6-hydroxyindole | 2 g |
| Potassium iodide | 2 g |
| Ethyl alcohol | 10 g |
| Xanthan gum sold by the company RHONE POULENC under the name RHODOPOL 23 SC | 2 g |
| Glycoside alkyl ether sold at a concentration of 60% AS by the company SEPPIC under the name TRITON CG 110 | 2.1 g AS |
| Water qs | 100 g |
| Natural pH 5.9 | |

The hair is towel-dried and rinsed with water, and a 12.5-volumes solution of hydrogen peroxide at pH 3 is then applied, the hair being massaged for 5 minutes.

After rinsing with water, a natural dark chestnut colour is obtained.

AS=active substance.

EXAMPLE 6

Hair that is 90% white is dyed by successively applying two compositions without performing intermediate rinsing.

The hair is impregnated for 5 minutes with the following composition:

| | |
|---|---|
| 5,6-Bis(trimethylsilyloxy)indole | 2 g |
| Potassium iodide | 2 g |
| Ethyl alcohol qs | 100 g |

The hair is towel-dried and 12.5-volumes solution of hydrogen peroxide at pH 3 is then applied, the hair being massaged for 5 minutes.

After rinsing with water, an ash-blonde colour is obtained.

EXAMPLE 7

Hair that is 90% white is dyed by successively applying two compositions without performing intermediate rinsing.

The hair is impregnated for 5 minutes with the following composition:

| | |
|---|---|
| 5-(or 6-)Myristoyloxy-6-(or 5-)hydroxyindole | 2 g |
| Potassium iodide | 2 g |
| Ethylene glycol monoethyl ether qs | 100 g |

The hair is towel-dried and a 12.5-volumes solution of hydrogen peroxide at pH 3 is applied, the hair being massaged for 5 minutes.

After rinsing with water, a slightly silvery golden blonde colour is obtained.

EXAMPLE 8

Hair that is 90% white is dyed by successively applying two compositions without performing intermediate rinsing.

The hair is impregnated for 5 minutes with a gel of the following composition:

| | |
|---|---|
| 5,6-(Methylenedioxy)indole | 1 g |
| Potassium iodide | 1 g |
| Ethyl alcohol | 10 g |
| Xanthan gum sold by the company RHONE POULENC under the name RHODOPOL 23 SC | 2 g |
| Glycoside alkyl ether sold at a concentration of 60% AS by the company SEPPIC under the name TRITON CG 100 | 2.1 g AS |
| Water qs | 100 g |
| Natural pH 5.9 | |

The hair is towel-dried and 12.5-volumes solution of hydrogen peroxide at pH 3 is then applied, the hair being massaged for 5 minutes.

After the hair is rinsed with water, a very light ash-blonde colour is obtained.

EXAMPLE 9

Permanent-waved hair that is 90% white is dyed by successively applying two compositions without performing intermediate rinsing.

The hair is impregnated for 4 minutes with the following composition:

| | |
|---|---|
| 5-Acetoxy-6-hydroxyindole | 0.5 g |
| Potassium iodide | 0.5 g |
| Ethyl alcohol | 10.0 g |
| Sodium lauryl ether sulphate oxyethylenated with 2 moles of ethylene oxide | 4.5 g AS |
| Water qs | 100 g |
| pH 5.5 | |

Without performing intermediate rinsing, a 12.5-volumes solution of hydrogen peroxide at pH 3 is then applied, the hair being massaged for 5 minutes.

After rinsing with water, a slightly silvery, golden, very light blonde colour is obtained.

EXAMPLE 10

Natural hair that is 90% white is dyed by successively applying two compositions without performing intermediate rinsing.

The hair is impregnated for 5 minutes with a 10-volumes composition of hydrogen peroxide (A).

After towel-drying and without intermediate rinsing, a solution (B) having the following composition is applied:

| | |
|---|---|
| 5-Methoxy-6-hydroxyindole | 0.5 g |
| Potassium iodide | 0.5 g |
| Ethyl alcohol | 10.0 g |
| Water qs | 100 g |
| Natural pH 6.3 | |

By massaging the hair for 5 minutes, after rinsing with water, a medium grey colour is obtained.

EXAMPLE 11

Natural hair that is 90% white is dyed by successively applying two compositions.

The hair is impregnated for 15 minutes with the following composition:

| | |
|---|---|
| 3-Methyl-5,6-dihydroxyindole | 1.0 g |
| Sodium iodide | 1.0 g |
| Ethyl alcohol | 10.0 g |
| Water qs | 100 g |
| Natural pH 4.9 | |

After towel-drying and an intermediate rinse, a 20-volumes solution of hydrogen peroxide is applied, the hair being massaged for 5 minutes.

After rinsing with water, a bluish deep black colour is obtained.

EXAMPLE 12

Hair that is 90% white is dyed by successively applying two compositions without performing intermediate rinsing.

The hair is impregnated for 5 minutes with the following composition:

| | |
|---|---|
| 2-Ethoxycarbonyl-5,6-dihydroxyindole | 2.0 g |
| Potassium iodide | 2.0 g |
| Ethylene glycol monoethyl ether qs | 100 g |

The hair is towel-dried and a 10-volumes solution of hydrogen peroxide at pH 3 is then applied, the hair being massaged for 5 minutes.

After rinsing with water, a golden blonde colour is obtained.

EXAMPLE 13

Hair that is 90% white is dyed by successively applying two compositions without performing intermediate rinsing.

The hair is impregnated for 5 minutes with the following composition:

| | |
|---|---|
| 5-Hydroxy-6-methoxyindole | 2.0 g |
| Potassium iodide | 2.0 g |
| Ethylene glycol monoethyl ether qs | 100 g |

The hair is towel-dried and a 10-volumes solution of hydrogen peroxide at pH 3 is applied, the hair being massaged for 5 minutes.

After rinsing with water, a natural very dark blonde colour is obtained.

EXAMPLE 14

Hair that is 90% white is dyed by successively applying two compositions without performing intermediate rinsing.

The hair is impregnated for 5 minutes with the following composition:

| | |
|---|---|
| 5,6-Carbonyldioxyindole | 2.0 g |
| Potassium iodide | 2.0 g |
| Ethylene glycol monoethyl ether qs | 100 g |

The hair is towel-dried and a 10-volumes solution of hydrogen peroxide at pH 3 is then applied, the hair being massaged for 5 minutes.

After rinsing with water, a dark blonde (greenish-grey) colour is obtained.

EXAMPLE 15

Hair that is 90% white is dyed by successively applying two compositions without performing intermediate rinsing.

The hair is impregnated for 5 minutes with the following composition:

| | |
|---|---|
| 2-Carboxy-5,6-dihydroxyindole | 2.0 g |
| Potassium iodide | 2.0 g |
| Ethylene glycol monoethyl ether qs | 100 g |

The hair is towel-dried and a 10-volumes solution of hydrogen peroxide at pH 3 is then applied, the hair being massaged for 5 minutes.

After rinsing with water, a dark blonde colour is obtained.

EXAMPLE 16

Natural hair that is 90% white is dyed by successively applying two compositions (A) and (B) and performing intermediate rinsing.

The hair is impregnated for 5 minutes with the following composition (A):

| | |
|---|---|
| 2-Methyl-5,6-dihydroxyindole | 1 g |
| 5,6-Dihydroxyindole | 0.3 g |
| Potassium iodide | 0.5 g |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g AS |
| Triethanolamine qs pH 6.5 | |
| Water qs | 100 g |

After rinsing with water, a 12.5-volumes composition of hydrogen peroxide (B) is applied for 5 minutes.

After rinsing with water, a golden chestnut colour is obtained.

| 12.5-volumes COMPOSITION (B) | |
|---|---|
| Hydrogen peroxide | 3.75 g |
| Ammonium lauryl sulphate | 6.7 g |
| Gum arabic | 1 g |
| Stabilizer | 0.03 g |
| 2-Amino-2-methyl-1-propanol qs pH 4 | |
| Water qs | 100 g |

EXAMPLE 17

Natural hair that is 90% white is dyed by successively applying two compositions (A) and (B) and performing intermediate rinsing.

The hair is impregnated for 5 minutes with the following composition (A):

| | |
|---|---|
| 2-Ethoxycarbonyl-5,6-dihydroxyindole | 1.3 g |
| 5,6-Dihydroxyindole | 0.3 g |
| Potassium iodide | 1 g |
| Ethyl alcohol | 10 g |
| Guar gum sold by the company CELANESE under the name "JAGUAR HP 60" | 1 g |
| Glycoside alkyl ether sold at a concentration of 60% AS by the | 5 g AS |

| | |
|---|---|
| company SEPPIC under the name "TRITON CG 110" | |
| Triethanolamine qs pH 6.5 | |
| Water qs | 100 g |

After rinsing with water, a 12.5-volumes composition of hydrogen peroxide (B), as described in Example 16, is applied for 5 minutes.

After rinsing with water, a dark ash-blonde colour is obtained.

EXAMPLE 18

Natural hair that is 90% white is dyed by successively applying two compositions (A) and (B) and performing intermediate rinsing.

The hair is impregnated for 5 minutes with the following composition (A):

| | |
|---|---|
| 2,3-Dimethyl-5,6-dihydroxyindole | 0.8 g |
| 5,6-Dihydroxyindole | 0.3 g |
| Potassium iodide | 0.9 g |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g AS |
| Triethanolamine qs pH 6.5 | |
| Water qs | 100 g |

After rinsing with water, a 12.5-volumes composition of hydrogen peroxide (B), as described in Example 16, is applied for 5 minutes.

After rinsing with water, an ash-blonde colour is obtained.

EXAMPLE 19

Permanent-waved hair that is 90% white is dyed by successively applying two compositions (A) and (B) and performing intermediate rinsing.

The hair is impregnated for 5 minutes with the following composition (A):

| | |
|---|---|
| 5-Acetoxy-6-hydroxyindole | 0.8 g |
| 5,6-Dihydroxyindole | 0.4 g |
| Potassium iodide | 0.5 g |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g AS |
| Triethanolamine qs pH 6.5 | |
| Water qs | 100 g |

After rinsing with water, a 12.5-volumes composition of hydrogen peroxide (B), as described in Example 16, is applied for 5 minutes.

After rinsing with water, a dark chestnut colour is obtained.

EXAMPLE 20

Permanent-waved hair that is 90% white is died by successively applying two compositions (A) and (B) and performing intermediate rinsing.

The hair is impregnated for 10 minutes with the following composition (A):

| | |
|---|---|
| 2-Methyl-5,6-dihydroxyindole hydrobromide | 1 g |
| Ammonium iodide | 1 g |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g AS |
| Triethanolamine qs pH 6.6 | |
| Water qs | 100 g |

After rinsing with water, a 12.5-volumes composition of hydrogen peroxide (B), as described in Example 16, is applied for 5 minutes.

After rinsing with water, a slightly golden light chestnut colour is obtained.

EXAMPLE 21

Hair that is 90% white is dyed by successfully applying two compositions (B) and then (A) without performing intermediate rinsing.

The hair is impregnated for 10 minutes with the following composition (B):

| | |
|---|---|
| Potassium iodide | 1 g |
| Water qs | 100 g |
| Natural pH 6.9 | |

A composition (A) as follows, which is produced by mixing the following two compositions (A1) and (A2) in a 50:50 ratio at the time of use, is then applied:

| COMPOSITION (A1) | |
|---|---|
| 2,3-Dimethyl-5,6-dihydroxyindole hydrobromide | 1 g |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g AS |
| Water qs | 100 g |
| Natural pH 6.5 | |

COMPOSITION (A2)

7.5-volumes solution of aqueous hydrogen peroxide, pH 3.5.

Composition (A) is left in place for 10 minutes and the hair is then rinsed with water.

The hair is dyed a pearly beige blonde.

EXAMPLE 22

Hair that is 90% white is dyed by successively applying two compositions (A) and then (B), without performing intermediate rinsing.

The hair is impregnated for 10 minutes with the following composition (A), which is produced by mixing the following two compositions (A1) and (A2) in a 50:50 ratio at the time of use:

| COMPOSITION (A1) | |
|---|---|
| 2,3-Dimethyl-5,6-dihydroxyindole | 1 g |

-continued

COMPOSITION (A1)

| | |
|---|---|
| hydrobromide | |
| Ethyl alcohol | 10 g |
| Guar gum sold by the company CELANESE under the name "JAGUAR HP 60" | 1 g |
| Glycoside alkyl ether sold at a concentration of 60% AS by the company SEPPIC under the name "TRITON CG 110" | 5 g |
| Water qs | 100 g |
| Natural pH 6.5 | |

COMPOSITION (A2)

30-volumes solution of aqueous hydrogen peroxide, pH 3

The following composition (B) is then applied:

| | |
|---|---|
| potassium iodide | 1 g |
| Water qs | 100 g |
| Natural pH 6.9 | |

The composition (B) is left in place for 10 minutes and the hair is then rinsed with water. The hair is dyed a pearly beige blonde.

We claim:

1. A process for dyeing human keratinous fibers comprising applying to said fibers at least one composition (A) comprising, in a cosmetically acceptable medium at least one indole derivative having the formula

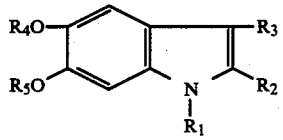

(I)

wherein
  $R_1$ represents hydrogen, $C_1-C_6$ lower alkyl or $-SiR_9R_{10}R_{11}$,
  $R_2$ and $R_3$, each independently, represent hydrogen, $C_1-C_6$ lower alkyl, carboxyl, lower alkoxycarbonyl wherein the alkoxy moiety contains 1-6 carbon atoms or $-COOSiR_9R_{10}R_{11}$,
  $R_4$ and $R_5$, each independently, represent hydrogen, $C_1-C_{20}$ linear or branched alkyl, formyl, linear or branched $C_2-C_{20}$ acyl, linear or branched $C_3-C_{20}$ alkenoyl, $-SiR_9R_{10}R_{11}$, $-P(O)(OR_6)_2$ or $R_6OSO_2-$, or $R_4$ and $R_5$ together with the oxygen atoms to which they are attached form a ring containing or not a carbonyl group, a methylene group, a thiocarbonyl group, a $>P(O)OR_6$ group or a $>CR_7R_8$ group,
  $R_6$ and $R_7$ represent hydrogen or $C_1-C_6$ lower alkyl,
  $R_8$ represents $C_1-C_6$ lower alkoxy, monoalkylamino wherein the alkyl moiety has 1-6 carbon atoms or dialkylamino wherein the alkyl moiety has 1-6 carbon atoms,
  $R_9$, $R_{10}$ and $R_{11}$, each independently, represent $C_1-C_6$ linear or branched alkyl,
  with the proviso that at least one of $R_1-R_5$ is other than hydrogen,
  the inorganic or organic acid addition salts of said indole and the corresponding alkali metal, alkaline earth metal and amine salts thereof,
  said indole being present in an amount ranging from 0.01 to 5 percent by weight based on the total weight of said composition, and
  (a) an iodide present in an amount ranging from 0.007 to 4 percent by weight based on the total weight of said composition and expressed as iodide ions, or
  (b) a solution of hydrogen peroxide at a concentration of 1–40 volumes, said composition (A) having a pH ranging from 3.5 to 7 when said cosmetically acceptable medium is water or a water solvent mixture,
  said composition (A) being applied to said human keratinous fibers either prior to or subsequent to the application to said keratinous fibers of a composition (B) comprising, in a cosmetically acceptable medium, (i) hydrogen peroxide solution at a pH ranging from 2 to 7 when said composition (A) contains said iodide, or (ii) said iodide when said composition (A) contains hydrogen peroxide.

2. The process of claim 1 wherein said indole has the formula

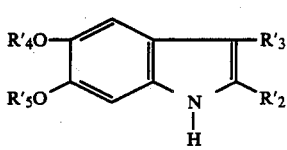

(II)

wherein
  $R'_2$ and $R'_3$, each independently, represent hydrogen, $C_1-C_6$ lower alkyl, $C_1-C_6$ carboxyl, lower alkoxy carbonyl wherein the alkoxy moiety contains 1-6 carbon atoms,
  $R'_4$ and $R'_5$, each independently, represent hydrogen, $C_1-C_6$ alkyl, $C_2-C_{20}$ linear acyl, or trimethylsilyl, or
  $R'_4$ and $R'_5$ together with the oxygen atoms to which they are attached form a methylenedioxy or carbonyldioxy ring.

3. The process of claim 1 wherein said indole derivative is selected from the group consisting of
  5-methoxy-6-hydroxyindole,
  3-methyl-5,6-dihydroxyindole,
  2-methyl-5,6-dihydroxyindole,
  5,6-bis (trimethylsilyloxy) indole,
  5-(or 6-) myristoyloxy-6-(or 5-) hydroxyindole,
  5,6-(methylenedioxy) indole,
  5-acetoxy-6-hydroxyindole,
  2-ethoxycarbonyl-5,6-dihydroxyindole,
  5-hydroxy-6-methoxyindole,
  5,6-carbonyldioxyindole and
  2-carboxy-5,6-dihydroxyindole.

4. The process of claim 1 wherein said iodide is an alkali metal iodide, an alkaline earth metal iodide or an ammonium iodide.

5. The process of claim 1 comprising, in a first stage, applying to said human keratinous fibers said composition (A) containing an iodide selected from the group consisting of an alkali metal iodide, an alkaline earth metal iodide or an ammonium iodide and at least one said indole derivative and, in a second stage applying to said human keratinous fibers, said composition (B) containing hydrogen peroxide.

6. The process of claim 1 wherein said human keratinous fibers are rinsed with water after the application of said composition (A) and before the application of said composition (B).

7. The process of claim 1 wherein said composition (A) and said composition (B) are permitted to remain in contact with said human keratinous fibers for a period of time ranging from ten seconds to 45 minutes.

8. The process of claim 1 wherein said composition (A) and said composition (B) are in the form of a gel, a cream or an emulsion.

9. The process of claim 1 wherein said cosmetically acceptable medium is water, a solvent selected from the group consisting of ethyl alcohol, isopropyl alcohol, tert. butyl alcohol, ethylene glycol monomethyl ether, ethylene glycol monoethyl ether, ethylene glycol monobutyl ether and ethylene glycol monoethyl ether acetate, or a mixture of water and said solvent.

10. The process of claim 9 wherein said solvent is present in an amount ranging from 0.5 to 75 percent by weight based on the total weight of said composition.

11. The process of claim 1 wherein said cosmetically acceptable medium of said composition (B) containing said iodide is water or a solvent, water mixture and has a pH ranging from 3 to 11.

12. The process of claim 1 wherein one or both of said compositions (A) and (B) also contain at least one of an anionic, cationic, nonionic or amphoteric surfactant, present in an amount ranging from 0.1 to 50 percent by weight based on the total weight of said composition.

13. The process of claim 1 wherein one or both of said compositions (A) and (B) contain a thickening agent present in an amount ranging from 0.1 to 5 percent by weight based on the total weight of said composition.

14. A composition for dyeing human keratinous fibers comprising in a cosmetically acceptable medium at least one indole derivative having the formula

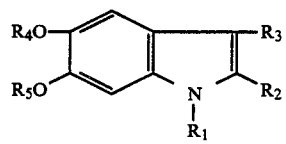

(I)

wherein
- $R_1$ represents hydrogen, $C_1$–$C_6$ alkyl or —$SiR_9R_{10}R_{11}$,
- $R_2$ and $R_3$, each independently, represent hydrogen, $C_1$–$C_6$ lower alkyl, carboxyl, lower alkoxycarbonyl wherein the alkoxy moiety contains 1–6 carbon atoms or —$COOSiR_9R_{10}R_{11}$,
- $R_4$ and $R_5$, each independently, represent hydrogen, $C_1$–$C_{20}$ linear or branched alkyl, formyl, linear or branched $C_2$–$C_{20}$ acyl, linear or branched $C_3$–$C_{20}$ alkenoyl, —$SiR_9R_{10}R_{11}$, —$P(O)(OR_6)_2$ or $R_6OSO_2$—, or $R_4$ and $R_5$ together with the oxygen atoms to which they are attached form a ring containing or not a carbonyl group, a methylene group, a thiocarbonyl group, a $>P(O)OR_6$ group or a $>CR_7R_8$ group,
- $R_6$ and $R_7$ represent hydrogen or $C_1$–$C_6$ lower alkyl,
- $R_8$ represents $C_1$–$C_6$ lower alkoxy, monoalkylamino wherein the alkyl moiety has 1–6 carbon atoms or dialkylamino wherein the alkyl moiety has 1–6 carbon atoms,
- $R_9$, $R_{10}$ and $R_{11}$, each independently, represent $C_1$–$C_6$ linear or branched alkyl, with the proviso that at least one of $R_1$–$R_5$ is other than hydrogen,
the inorganic or organic acid addition salts of said indole and the corresponding alkali metal, alkaline earth metal and amine salts thereof,
said indole being present in an amount ranging from 0.01 to 5 percent by weight based on the total weight of said composition, and
an iodide present in an amount ranging from 0.007 to 4 percent by weight based on the total weight of said composition and expressed as iodide ions.

15. The composition of claim 14 wherein said cosmetically acceptable medium contains water and has a pH ranging from 3.5 to 7.

16. The composition of claim 14 wherein said indole derivative has the formula

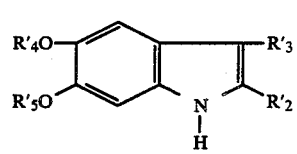

(II)

wherein
- $R'_2$ and $R'_3$, each independently, represent hydrogen, $C_1$–$C_6$ lower alkyl, $C_1$–$C_6$ carboxyl, lower alkoxy carbonyl wherein the alkoxy moiety contains 1–6 carbon atoms,
- $R'_4$ and $R'_5$, each independently, represent hydrogen, $C_1$–$C_6$ alkyl, $C_2$–$C_{20}$ linear acyl, or trimethylsilyl, or
- $R'_4$ and $R'_5$ together with the oxygen atoms to which they are attached form a methylenedioxy or carbonyldioxy ring.

17. The composition of claim 14 wherein said indole derivative is selected from the group consisting of
5-methoxy-6-hydroxyindole,
3-methyl-5,6-dihydroxyindole,
2-methyl-5,6-dihydroxyindole,
5,6-bis (trimethylsilyloxy) indole,
5-(or 6-) myristoyloxy-6-(or 5-) hydroxyindole,
5,6-(methylenedioxy) indole,
5-acetoxy-6-hydroxyindole,
2-ethoxycarbonyl-5,6-dihydroxyindole,
5-hydroxy-6-methoxyindole,
5,6-carbonyldioxyindole and
2-carboxy-5,6-dihydroxyindole.

18. The composition of claim 14 wherein said iodide is an alkali metal iodide, an alkaline earth metal iodide or ammonium iodide.

19. The composition of claim 14 which also contains 5,6-dihydroxyindole.

20. A multi-compartment kit for dyeing human keratinous fibers comprising a first compartment containing the composition of claim 14 and a second compartment containing a solution of hydrogen peroxide at a pH ranging from 2 to 7.

21. A multi-compartment kit for dyeing human keratinous fibers comprising a first compartment containing an iodide in amount ranging from 0.007 to 4 percent by weight based on the total weight of the composition and expressed as iodide ions in a cosmetically acceptable medium, a second compartment containing in a cosmetically acceptable medium an indole derivative having the formula

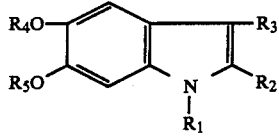

(I)

wherein
- $R_1$ represents hydrogen, $C_1$–$C_6$ lower alkyl or —$SiR_9R_{10}R_{11}$,
- $R_2$ and $R_3$, each independently, represent hydrogen, $C_1$–$C_6$ lower alkyl, carboxyl, lower alkoxycarbonyl wherein the alkoxy moiety contains 1–6 carbon atoms or —$COOSiR_9R_{10}R_{11}$,
- $R_4$ and $R_5$, each independently, represent hydrogen, $C_1$–$C_{20}$ linear or branched alkyl, formyl, linear or branched $C_2$–$C_{20}$ acyl, linear or branched $C_3$–$C_{20}$ alkenoyl, —$SiR_9R_{10}R_{11}$, —$P(O)(OR_6)_2$ or $R_6OSO_2$—, or $R_4$ and $R_5$ together with the oxygen atoms to which they are attached form a ring containing or not a carbonyl group, a methylene group, a thiocarbonyl group, a >$P(O)OR_6$ group or a >$CR_7R_8$ group,
- $R_6$ and $R_7$ represent hydrogen or $C_1$–$C_6$ lower alkyl,
- $R_8$ represents $C_1$–$C_6$ lower alkoxy, monoalkylamino wherein the alkyl moiety has 1–6 carbon atoms or dialkylamino wherein the alkyl moiety has 1–6 carbon atoms,
- $R_9$, $R_{10}$ and $R_{11}$, each independently, represent $C_1$–$C_6$ linear or branched alkyl,
- with the proviso that at least one of $R_1$–$R_5$ is other than hydrogen,
- the inorganic or organic acid addition salts of said indole and the corresponding alkali metal, alkaline earth metal and amine salts thereof,
- said indole being present in an amount ranging from 0.01 to 5 percent by weight based on the total weight of said composition,
- and a third compartment containing a 1–40 volume solution of hydrogen peroxide at a pH ranging from 2 to 7, the contents of said third compartment designed to be mixed with the contents of said second compartment at the time of use.

* * * * *